United States Patent [19]

Konishi

[11] Patent Number: 5,013,558
[45] Date of Patent: May 7, 1991

[54] PHARMACEUTICAL TREATMENTS FOR CEREBRAL AND NEURONAL DISEASES

[75] Inventor: Jin-emon Konishi, Hyogo, Japan

[73] Assignee: Nippon Zoki Pharmaceutical Co., Ltd., Osaka, Japan

[21] Appl. No.: 366,704

[22] Filed: Jun. 15, 1989

[30] Foreign Application Priority Data

Jun. 20, 1988 [JP] Japan .................. 63-152492

[51] Int. Cl.⁵ .............................. A61K 35/00
[52] U.S. Cl. ..................... 424/520; 424/574
[58] Field of Search ............ 424/95, 520, 574

[56] References Cited

FOREIGN PATENT DOCUMENTS 0101515  9/1978  Japan ........................... 424/95
0118711  7/1984  Japan ........................... 424/95

OTHER PUBLICATIONS

Sprumont in Experimentia 43:671 (1987).
Morita et al., "Differential Action of Nerve Growth Factor, Cyclic Amp & Neurotropin on PC12h Cells" Cell Structure & Function 13, 227–234 (1988).
Dan et al., "The Effect of Nerve Blocks & Combination of Drugs on Post Herpetic Neuralgia" JPN J Anesthesiol 30(3) 1981, pp. 285–290.

*Primary Examiner*—Douglas W. Robinson
*Assistant Examiner*—Jean Witz
*Attorney, Agent, or Firm*—Armstrong, Nikaido, Marmelstein, Kubovcik & Murray

[57] ABSTRACT

The present invention relates to pharmaceutical compositions for cerebral and neuronal diseases containing physiologically active substances extracted from infected tissues. The physiologically active substances of the present invention have NGF-like nerve growth stimulating effect. Therefore, the substances of the invention are useful as drugs for various cerebral and neuronal diseases such as dementia, post-herpetic neuralgia, brain edema and spino-cerebellar degeneration.

2 Claims, No Drawings

PHARMACEUTICAL TREATMENTS FOR CEREBRAL AND NEURONAL DISEASES

BACKGROUND OF THE INVENTION

The present invention relates to pharmaceutical compositions for cerebral and neuronal diseases containing physiologically active substances extracted from infected tissues.

Nerve Growth Factor (NGF) has biological activities stimulating differentiation and growth of sympathetic and sensory neurons. Relation between NGF and neuronal diseases at peripheral nerve has been suggested for long time, therefore NGF has been put up as a candidate for drugs to treat those diseases. Recently, it has also become clear that NGF is produced and performs functions at brain. Correlation between NGF and the cause of Alzheimer's senile dementia has been focused, and it is much expected to use NGF as a drug for dementia. However, since NGF is a proteinic factor, there are many problems such as administration route and pharmaceutical dosage form at administration of NGF to human. Therefore, it has been desired to develop drugs having nerve growth stimulating effect as NGF, which can be easily administered to human as well as having greater safety without any side effects.

As a result of investigations concerning physiologically active substances extracted from infected tissues and produced by inoculation with a poxvirus to animal tissues, organs or cultured cells. The substances have been found having excellent NGF-like action on nerve system.

An object of the present invention is to provide pharmaceutical compositions for cerebral and neuronal diseases containing physiologically active substances extracted from infected tissues. Another object of the invention is to provide a method for treating neuronal diseases in mammals which comprises administering an effective amount of physiologically active substances extracted from infected tissues.

DETAILED DESCRIPTION OF THE INVENTION

The physiologically active substances of the present invention can be prepared as follows:

(1) Infected tissues are homogenized with an extraction medium, and tissue fragments are removed.

(2) Extracted solution thus obtained is subjected to treatment to remove proteins.

(3) An adsorbent is added to the deproteinized solution, and then the material adsorbed onto the adsorbent is eluted.

The term "infected tissues" as used in this specification is defined as meaning: animal tissues, organs or cultured cells inoculated or infected with a poxvirus.

A poxvirus, for example, orthopoxvirus such as vaccinia virus, cowpox virus, variola virus, infectious ectromelia virus or monkeypox virus, parapoxvirus such as orf virus, paravaccinia virus or bovine papular stomatitis virus, capricopoxvirus such as sheeppox virus, goatpox virus or lumpy skin disease virus, avipoxvirus such as fowlpox virus or hare fibroma virus, leporipoxvirus such as rabbit myxoma virus or rabbit fibroma virus, swinepoxvirus, Yaba monkey tumor virus or Tarapox virus, can be used.

To obtain the infected tissues, various kinds of animals or birds can be utilized, for example, rabbit, sheep, goat, pig, cow, horse, monkey, hamster, guinea pig, rat, mouse or hen can be employed. The animal or bird can be selected according to a specie of poxvirus and other conditions. Also any kind of cultured cell, in which the selected poxvirus can multiply, is available, for example, cultured cell or tumor cell of kidney, skin, lung, testis, liver, muscle, adrenal, thyroid gland, brain, nerve cell or blood cell of rabbit, sheep, goat, pig, cow, horse, monkey, hamster, guinea pig, rat, mouse, hen or their embryo, cultured cell derived from human such as Hela cell, or decidua of the hatching egg can be employed.

The infected tissues are collected under aseptic conditions and ground to as small a size as possible. An extraction medium is added to the ground material which is then homogenized. As an extraction medium, distilled water, physiological saline, weakly acidic or basic buffer etc. may be used, and if desired, a stabilizer such as glycerin, a disinfectant or preservative such as phenol, or an inorganic salt such as sodium chloride, potassium chloride or magnesium chloride can be added to the medium. At that time, the extraction can be facilitated by a procedure to disintegrate cell tissues, such as freeze-thaw extraction, sonication or treatment with a detergent or an enzyme dissolving cell membrane.

The resulting emulsion is filtered or centrifuged to remove tissue fragments. The filtrate or supernatant is deproteinized which can be carried out according to a known method, for example, heating, sonication, treatment with a protein-denaturant such as an acid, a base, urea, guanidine, an organic solvent or a detergent, isoelectric point precipitation or salting-out technique. Subsequently, the denatured proteins thereby precipitated are removed by filtration using a filter paper such as cellulose or nitrocellulose, a glass filter, sellaite, Seitz's filter etc., ultrafiltration, gel filtration, ion-exchange chromatography or centrifugation.

The resulting extract containing the active substances is acidified, preferably to pH 3.5-5.5, by addition of an acid such as hydrochloric acid, sulfuric acid or hydrobromic acid, and then subjected to adsorption to an adsorbent such as active carbon, kaolin or an ion-exchange resin. The adsorbent can be added to the extracted solution and it is stirred, or the extracted solution can be passed through a column of the adsorbent.

To elute the material containing the active substances of the present invention, a basic solution is added to the adsorbent, preferably adjusting the suspension to pH 9-12, and then the mixture is incubated or stirred at room temperature or at a suitable temperature above room temperature by heating. The elution is achieved by removing the absorbent according to a known method such as filtration or centrifugation. The eluate thus obtained, preferably after adjusting it to pH 6.5-8.5, was concentrated to dryness under reduced pressure or lyophilized to give the active substances of the present invention.

The physical and chemical properties of the physiologically active substances obtained in the above preparation are as follows:

(1) Appearance:
Pale yellowish brown and hygroscopic powder.
(2) Solubility:
Soluble in water, methanol and ethanol.
(3) Ultraviolet adsorption: $\lambda max = 255-275$ nm.
(4) Ninhydrine reaction: Positive.
(5) One ml of perchloric acid is added to 2 mg of the substances of the present invention, and is heated until the solution become colorless. 3 ml of dilute hydrochloric acid, 0.4 g of amidol hydrochloride and 8 g of sodium hydrogen sulfite are dissolved in 100 ml of water, and then 2 ml of the resulting aqueous solution, 1 g of ammonium molybdate and 30 ml of water are mixed. 2 ml of the mixture is added to the above solution containing the substances of the present invention. Finally the solution show a blue color.

(6) 5 mg of the substances of the present invention is dissolved in 10 ml of water. 0.2 g of orcine and 0.135 g of iron(II)ammonium sulfate are dissolved in 5 ml of ethanol, 83 ml of hydrochloric acid is added to the mixture, and water was added until the total becomes 100 ml. 3 ml of the resulting mixture is added to 1 ml of the above solution containing the substances of the invention, and heated in boiling water bath. Finally the solution show a green color.

(7) Silver nitrate reagent is added to the aqueous solution of the substances of the present invention. The precipitate is produced.

(8) Containing base of nucleic acids.

(9) Various methods of protein detection are negative.

EXAMPLES

The following examples, which are illustrative only and not intended to limit the scope of the invention, describe the preparation of the physiologically active substances of the present invention.

EXAMPLE 1

Vaccinia virus was inoculated to the skin of healthy adult rabbit. The inflamed skin was cut off under aseptic conditions and well ground. Aqueous phenol solution was added to this ground material and subjected to homogenization, and the emulsion was filtered by centrifugation. The resulting filtrate was adjusted to pH 4.5–5.5, and then heated in a stream of 100° C. steam. After removing proteins thereby precipitated by filtration, the filtrate was adjusted to pH 8.5–10.0 by addition of sodium hydroxide, heated at 100° C. and filtered. The filtrate was adjusted to pH 4.5 and 1.5% active carbon was added thereto. After stirring for 1 to 5 hrs, the suspension was filtered. Water was added to the resulting active carbon and the suspension was adjusted to pH 9.4–10.0 by addition of sodium hydroxide. The extraction procedure was carried out by stirring for 3–5 hrs at 60° C. The suspension was filtered to remove the active carbon. The filtrate was adjusted to near neutral pH, about pH 7, by addition of hydrochloric acid and concentrated to dryness under reduced pressure to give the substances of the present invention. The yield of the substances of the present invention is 1.5–2.0 g per 1 kg of infected skin-tissues.

EXAMPLE 2

Methanol was added to the active carbon adsorbing the substances of the present invention, which was obtained in the same manner as Example 1, and stirred for 1 hour. The mixture was filtered and the filtrate was concentrated to dryness under reduced pressure to the substances of the present invention. The yield is 4.0–6.0 g per 1 kg of infected skin-tissues.

The following descriptions serve to illustrative pharmaceutical studies of the substances of the present invention.

(1) Toxicity test

The physiologically active substances of the present invention were administered to male and female of mice and rats orally, subcutaneously, intraperitoneally and intravenously to carry out acute toxicity tests. $LD_{50}$ of the substances of this invention was more than 5,000 mg/kg at any route of administrations independently of species of animals and differences between the sexes.

As a result of subacute toxicity tests, no abnormality was observed at any organs. The reproduction tests showed no effect on pregnant animal, fetus, newborn and reproductivity of offspring ($F_1$).

(2) Nerve growth stimulating activity

The nerve growth stimulating activity of the physiologically active substances of the present invention was investigated by using PC12h cells (a rat pheochromocytoma cell line) which respond to NGF by differentiating into sympathetic neuron-like cells.

PC12h cells were planted in a collagen-coated 24-well microplate in DF medium containing 5% horse serum and 5% precolostrum newborn calf serum. After culturing overnight, the medium was replaced with a serum free medium (DF medium supplemented with human transferrin, bovine insuline and progesterone) with 100 μg/ml of the substances of the present invention and incubated for 3 days under 90% air and 10% $CO_2$ gas at 37° C. The rate of the number of cells with neurite process ($\geq 20$ μm) was determined by counting cells at random in 10 fields under a phase contrast microscope.

As a result, the substances of the present invention showed NGF-like neurotrophic activity as far as neurite outgrowth and cell surface change were concerned.

(3) Clinical study

The pharmaceutical compositions containing the substances of the present invention as an active ingredient were administered to patients suffering from post-herpetic neuralgia, brain edema, dementia and spino-cerebellar degeneration.

I. Post-herpetic neuralgia 8 mg of the substances of the present invention were administered twice a day orally to patients suffering from post-herpetic neuralgia for 4 weeks. The rate of more than slightly improvement was more than 63%, and moderate to marked improvement was observed in about half of patients.

II. Brain edema

To patients suffering from brain edema, 10 mg to 36 mg of the substances of the invention were administered daily for one to two weeks intravenously or by instillation. Subsequently, according to the condition of a patient, the treatment was continued by administering the substances of the invention orally 8 mg to 16 mg a day for a few weeks.

Efficacy of the treatment is checked by a time course comparison of edema size in using CT Scan and by observing symptoms in using a neurogial evaluation rating scale.

As a result at 10 day, comparing the efficacy of the substances of the present invention with that of steroid hormone therapy, the substances of this invention were significantly superior to steroid hormones, i.e. the improving rate of the treatment with the present substances was 63%, but it was 42% in case of steroid hormone therapy.

III. Dementia

The clinical studies were carried out in patients suffering from cerebral organic disorder, vascular dementia and Alzheimer's dementia. About 10 mg daily of the substances of the present invention were administered to the said patients intravenously or by instillation.

Efficacy was evaluated by Hasegawa's simple mental function evaluation scale, scoring degrees of psychopathologic conditions such as volition and emotion, scoring degrees of actions in daily life (ADL), clinical test such as EEG and CT scan, and GBS scale (a rating scale for dementia syndromes).

In patients treated with the substances of the present invention for 8 weeks, more than about 70% cases showed the efficacy improving motility, volition, speech disorder, attention, memory, incontinence, emotional disorder and the like.

IV. Spino-cerebellar degeneration 3 mg to 8 mg daily of the substances of the present invention were administered intravenously to 4 members of a family with spino-cerebellar degeneration. 2 patients were at a terminal stage and unaffected by the treatment. In the 2 remaining cases, where the disease was evolutive, a spectacular improvement was observed on the symptoms such as incentinence, motor incoordination, defective vision, nocturnal spasm and ataxic gait. The effect became evident after about 2 months of this treatment.

In one evolutive case, treatment was discontinued for 2 weeks. All pathological symptoms, reappeared during that period, were disappeared again at resumption of the treatment of the substances of the present invention.

Furthermore, in the said clinical trials, severe side effect was not found at all, and few side effects such as sleeplessness, sweating, thirst and gastrointestinal disorders were observed.

As shown by the above-mentioned results, the physiologically active substances of the present invention have NGF-like nerve growth stimulating effect, and consequently can repair cerebral and nerve cells which are injured or which physiological function decreases. Therefore, the substances of the invention are useful as drugs for vascular dementia caused by cerebral arteriosclosis, postencephalitis, postapopletic disorder or post traumatic syndrome after head injury, Alzheimer's disease including Alzheimer's senile dementia, subcortical dementia such as Huntington's chorea or Parkinson's disease, cerebral diseases such as brain edema and spino-cerebellar degeneration, and neuronal diseases such as autonomic imbalance and post-herpetic neuralgia caused by morbidity or injury of sympathetic nerve or sensory nerve.

The substances of the invention have low toxicity and great safety, so that their long-term continuous administration and oral use are possible.

The substances of the present invention can be made into pharmaceutical compositions by combination with appropriate medicinal carriers or diluents, and can be formulated into preparations in solid, semisolid, liquid or gaseous form such as tablets, capsules, powders, granules, solutions and suppositories in usual ways for oral or parenteral administrations.

In pharmaceutical dosage forms, the substances of the present invention can be used alone or in appropriate association, as well as in combination with other pharmaceutically active components.

In case of oral preparations, the substances can be used alone or combined with appropriate additives to make tablets, powders, granules or capsules, e.g. with conventional additives such as lactose, mannitol, corn starch or potato starch; with binders such as crystalline cellulose, cellulose derivatives, acacia, corn starch or gelatins; with disintegrators such as corn starch, potato starch or calcium carboxymethylcellulose; with lubricants such as talc or magnesium stearate; and if desired, with diluents, buffering agents, moistening agents, preservatives and flavoring agents.

The substances of the present invention can be formulated into a preparations for injections by dissolving, suspending or emulsifying in aqueous or nonaqueous solvent, such as distilled water for injection, physiologically saline solution, 5–20% glucose aqueous solution, vegetable oil, synthetic aliphatic acid glycerides, esters of higher aliphatic acid or propylene glycol; and if desired, with conventional additives such as solubilizers, isotonic agents, suspending agents, emulsifying agents, stabilizers and preservatives. Also the substances of the present invention can be formulated into lyophilized preparations in vials, which are used as injections by dissolving with the said solvent.

Furthermore, the substances of the invention can be made into a suppository by mixing with a variety of bases, e.g. emulsifying base or water-soluble base, and also can be made into inhalations or aerosol preparations.

The desirable dose of the substances of the present invention varies with the subject, form of the drug, method and period of administration. However, in order to obtain desirable effects, generally it is recommended to administer orally 1 to 100 mg, preferably 4 to 40 mg daily.

In case of parenteral administrations e.g. injections, doses of the substances in the order of one tenth to one third of the above dose are preferable as daily doses.

Some prescriptions of the pharmaceutical compositions are shown below as examples which contain the substances of the present invention as an active ingredient.

| Prescription example 1 (tablet) | |
|---|---|
| Component | Content in a tablet (mg) |
| substances of this invention | 4 |
| lactose | 106 |
| crystalline cellulose | 40 |
| calcium carboxymethylcellulose | 20 |
| magnesium stearate | 10 |
| | Total 180 mg |

| Prescription example 2 (capsule) | |
|---|---|
| Component | Content in a capsule (mg) |
| substances of this invention | 10 |
| lactose | 200 |
| talc | 40 |
| | Total 250 mg |

| Prescription example 3 (injection) | |
|---|---|
| Component | Content in an ampule (mg) |
| substances of this invention | 1 |
| sodium chloride | proper amount |
| distilled water for injection | proper amount |
| | Total 1 ml |

What is claimed is:

1. A method for treating spino-cerebellar degeneration, which comprises administering to a patient in need of such treatment an effective amount of a protein-free extract of infected tissues inoculated with a poxvirus, said extract having the following physical and chemical properties:

pale yellowish-brown, hygroscopic powder;
soluble in water, methanol and ethanol;
ultraviolet adsorption, $\lambda max = 255-275$ nm;
positive ninhydrin reaction;

gives a blue color with amidol and ammonium molybdate;

gives a green color with orcin and iron (II) ammonium sulfate;

gives a precipitate with silver nitrate; and contains nucleic acid bases.

2. A method for treating dementia, which comprises administering to a patient in need of such treatment an effective amount of a protein-free extract of infected tissues inoculated with a poxvirus, said extract having the following physical and chemical properties:

pale yellowish-brown, hygroscopic powder;

soluble in water, methanol and ethanol;

ultraviolet adsorption, $\lambda max = 255-275$ nm;

positive ninhydrin reaction;

gives a blue color with amidol and ammonium molybdate;

gives a green color with orcin and iron (II) ammonium sulfate;

gives a precipitate with silver nitrate; and contains nucleic acid bases.

* * * * *